US00PP21946P2

(12) United States Plant Patent
Heims

(10) Patent No.: US PP21,946 P2
(45) Date of Patent: May 31, 2011

(54) ***BEGONIA* PLANT NAMED 'SILVER SPLENDOR'**

(50) Latin Name: ***Begonia* hybrid**
Varietal Denomination: Silver Splendor

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 39 days.

(21) Appl. No.: 12/592,236

(22) Filed: Nov. 20, 2009

(51) Int. Cl.
*A01H 5/00* (2006.01)

(52) U.S. Cl. ..... Plt./343
(58) Field of Classification Search ..... Plt./343
See application file for complete search history.

(56) References Cited

U.S. PATENT DOCUMENTS

PP19,567 P2 * 12/2008 Heims ..... Plt./343
* cited by examiner

*Primary Examiner* — June Hwu
(74) *Attorney, Agent, or Firm* — Klarquist Sparkman, LLP

(57) ABSTRACT

A new and distinct form of *Begonia* plant characterized by deeply cut maple-shaped leaves, heavily silver-spotted foliage, and vigor.

1 Drawing Sheet

Botanical denomination: *Begonia* hybrid.
Variety designation: 'Silver Splendor'.
Parentage: *Begonia hemsleyana*×*Begonia taliensis.*

BACKGROUND OF THE INVENTION:

The present invention relates to a new and distinct cultivar of *Begonia*, of the family Begoniaceae, and given the cultivar name, 'Silver Splendor'. This plant originated from planned cross between *Begonia hemsleyana*, as the seed parent, and *Begonia taliensis*, as the pollen parent. All the seedlings in the cross had slightly different versions of deeply divided maple shaped leaves. This selection was made for its deeply cut maple-shaped leaves, heavily silver-spotted foliage, and vigor. This combination of traits is unique in Zone 7 hardy *Begonia.*

Compared to the seed parent *Begonia hemsleyana*, the new cultivar has leaves that are heavily silver-spotted and blotched between the veins rather than plain green to lightly spotted and leaves that are simple and deeply palmately divided rather than palmately lobed. Compared to the pollen parent, *Begonia taliensis*, the new cultivar is taller with leaves that are deeply palmately divided rather than shallowly palmately lobed.

Compared to *Begonia* 'Metallic Mist', U.S. Plant Pat. No. 19,567, the new cultivar is taller with the leaves more deeply cut and less silvered. The flowers on the new cultivar are a darker pink.

The new variety has been reproduced only by asexual propagation (cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS:

FIG. 1 shows a close up of the flowers and leaf of *Begonia* 'Silver Splendor'.

FIG. 2 shows a 1-and-a-half year old plant in a growing in a one gallon container in August in Canby. Oreg.

DETAILED PLANT DESCRIPTION

The following is a detailed description of the new *Begonia* cultivar based on observations of a one-year-old specimen grown in the ground in a shade house in September in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $4^{th}$ edition.

Plant:
- *Type.*—Herbaceous rhizomatous perennial.
- *Form.*—Clumping, caulescent.
- *Cold hardiness.*—USDA Zone 7.
- *Size.*—Grows to 50 cm tall to top of foliage and 45 cm wide.
- *Vigor.*—Excellent.

Stem:
- *Size.*—Grows to 45 cm long and 12 mm wide.
- *Internodes.*—From 1 to 16 cm long.
- *Surface.*—Pubescent.
- *Color.*—Greyed Orange 165A.

Leaf:
- *Type.*—Simple.
- *Arrangement.*—Alternate.
- *Shape.*—Broadly ovate overall.
- *Lobing /Division.*—Irregularly palmately lobed, 4 to 7 main lobes, terminal lobes often cut to the base and sometimes stalked.
- *Venation.*—Palmate.
- *Margins.*—Toothed.
- *Apex.*—Acute.
- *Base.*—Cordate.
- *Blade size.*—Grows to 17 cm wide and 21 cm long.
- *Surface texture.*—Scabrous on top and bottom.
- *Bracts.*—Deciduous, lanceolate, 27 mm long and 10 mm wide, entire, acuminate, glabrous on both surfaces, Yellow Green 146B with veins Greyed Purple 183A.

*Petiole description.*—Grows to 23 cm long and 7 mm wide, succulent, pubescent, Grayed Orange 176A speckled with very narrow and 2 to 4 mm long lines of Yellow Green 145A.

*Leaf color.*—Top side closest to Green 139A with interveinal spotting or blotching of silver, Black 202D; bottom side Yellow Green 148A with Greyed Purple 183A on and around the veins.

Inflorescence:

*Type.*—Axillary, bisexual, cymose.

*Number of flowers per cyme.*—4 to 6.

*Peduncle description.*—Grows 11 cm long and 4 mm wide, glabrous, fleshy, Greyed Red 178A; with 2 opposite, dehiscent petiolate leaf-bracts below each cyme, which grow to 11 mm wide and 26 mm long, margins entire on the bottom half and irregularly incised on the top half, glabrous, Yellow Green 146B with veins Greyed Purple 183A.

*Pedicel description.*—About 5 mm long, 1.1 mm wide, fleshy, glabrous, Greyed Purple 184A.

*Bloom period.*—Late summer in Canby, Oreg.

Flower bud:

*Size.*—Staminate flowers 7 mm long and 4 mm wide prior to maturation; pistillate flowers are 22 mm deep and 15 mm wide prior to opening.

*Color.*—Red Purple 58A on tepal area, Greyed Orange 166D on ovary.

Flower:

*Type.*—Monoecious, bilaterally symmetrical.

*Pistillate flower.*—Grows to 25 mm deep and 46 mm wide overall; 5 to 10 overlapping fleshy tepals, irregularly grow to 21 mm long and 14 mm wide, broadly elliptical to obovate, tip and base obtuse, margins entire to notched 1 to 3 times near tip, glabrous and Red Purple 65A on both sides; ovary to 18 mm wide and 20 mm deep, three winged, two equal and one longer, Yellow Green 153A darkening to Greyed Orange 174B, style 3 branched, stigma 2 branched and twisted, style and stigma 7 mm deep and 15 mm wide overall, Yellow Green 151A.

*Staminate flower.*—7 mm long and 4 mm wide, 4 to 8 overlapping tepals which remain in bud, 4 larger outer tepals 9 mm long and 5 mm wide and inner tepals grow to 6 mm long and 4 mm wide; all are cupped, broadly elliptical, entire, tip obtuse, base attenuate, Red Purple 58A inside and outside; stamen many in a globular head, Yellow 4A overall, filament less than 1 mm long, anthers less than 1 mm, pollen none.

*Fragrance.*—None.

*Lastingness.*—A cyme blooms for about 4 weeks on the plant.

Fruit and seed: None, sterile.

Diseases and pests: *Begonia* species are susceptible to root rots. This new variety has no known immunities.

I claim:

1. A new and distinct form of *Begonia* plant as hereby illustrated and described.

* * * * *

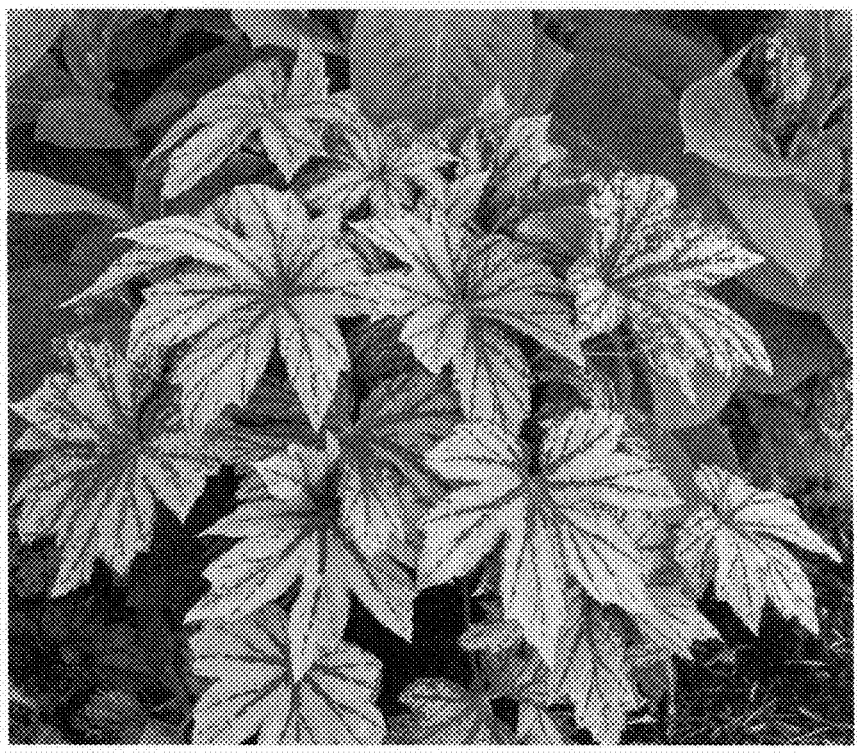

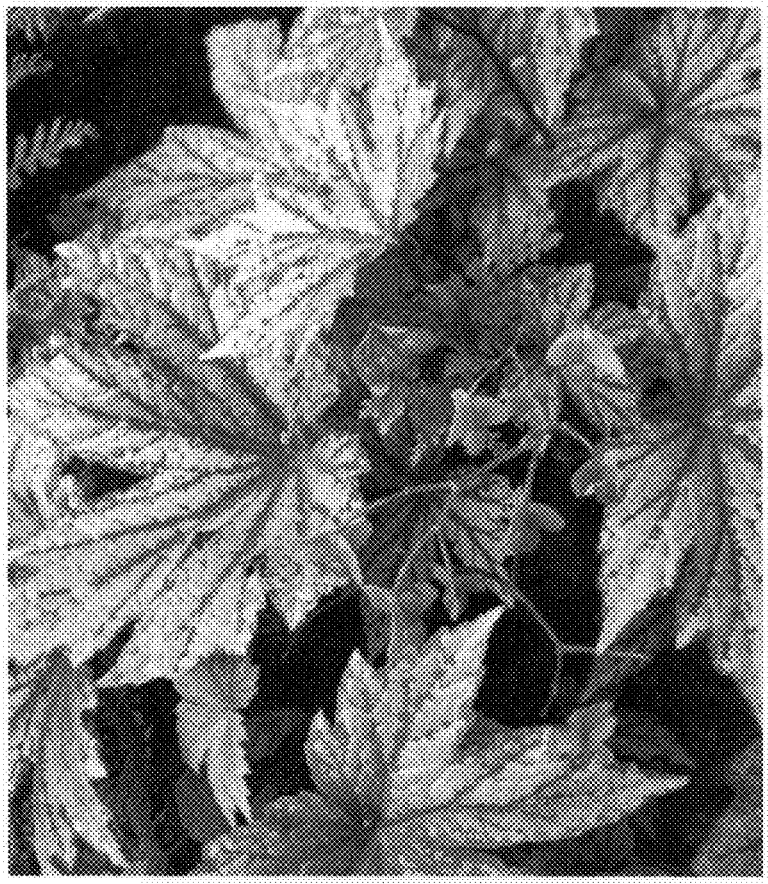
Figure 1 above, Figure 2 below